United States Patent [19]

Day et al.

[11] 4,148,809

[45] Apr. 10, 1979

[54] PROCESS FOR PREPARING DL-CIS-1-HYDROXY-3-SUBSTITUTED-6,6-DIMETHYL-6,6A,7,8,10,10A-HEXAHYDRO-9H-DIBENZO[B,D]PYRAN-9-ONES

[75] Inventors: William A. Day; Edward R. Lavagnino, both of Indianapolis, Ind.

[73] Assignee: Eli Lilly and Company, Indianapolis, Ind.

[21] Appl. No.: 831,453

[22] Filed: Sep. 8, 1977

Related U.S. Application Data

[63] Continuation-in-part of Ser. No. 702,809, Jul. 6, 1976, abandoned.

[51] Int. Cl.² ........................................... C07D 311/78
[52] U.S. Cl. .................................................. 260/345.3
[58] Field of Search ...................................... 260/345.3

[56] References Cited

U.S. PATENT DOCUMENTS 4,054,582  10/1977  Blanchard et al. ............... 260/345.3

OTHER PUBLICATIONS

Archer et al., J. Org. Chem., 42, 2277 (1977).
Razdan et al., Jacs, 96, 5860 (1974).
Razdan et al., Tetrahedron Letters, pp. 4947–4950 (1969).

*Primary Examiner*—Nicky Chan
*Attorney, Agent, or Firm*—Charles W. Ashbrook; Arthur R. Whale

[57] ABSTRACT

Reaction of a 5-substituted resorcinol with a 1-alkoxy-4-(1-hydroxy-1-methylethyl)-1,4-cyclohexadiene in the presence of a suitable catalyst affords the corresponding dl-cis-1-hydroxy-3-substituted-6,6-dimethyl-6,6a,7,8,10,10a-hexahydro-9H-dibenzo[b,d]pyran-9-one.

10 Claims, No Drawings

PROCESS FOR PREPARING DL-CIS-1-HYDROXY-3-SUBSTITUTED-6,6-DIMETHYL-6,6A,7,8,10,10A-HEXAHYDRO-9H-DIBENZO[B,D]PYRAN-9-ONES

CROSS REFERENCE TO RELATED APPLICATIONS

This is a continuation-in-part of application Ser. No. 702,809, filed July 6, 1976, now abandoned.

BACKGROUND OF THE INVENTION

The preparation of 1-hydroxy-3-substituted-6,6-dimethyl-6,6a,7,8,10,10a-hexahydro-9H-dibenzo[b,d]-pyran-9-ones has been reported by Fahrenholtz, Lurie and Kierstead, J. Am. Chem. Soc., 88, 2079 (1966), 89, 5934 (1967). The reported synthesis of such compounds included the reaction of a 5-substituted resorcinol with diethyl α-acetylglutarate to provide the corresponding ethyl 4-methyl-5-hydroxy-7-substituted coumarin-3-proprionate. Cyclization of the latter compound by reaction with a metal hydride afforded a 1-hydroxy-3-substituted-6,7,8,10-tetrahydro-6H-dibenzo[b,d]pyran-6,9-dione. The 9-ketone group was next protected by ketal formation, and then treatment of the ketal with methyl magnesium bromide, followed by deketalization, provided a 1-hydroxy-3-substituted-6,6-dimethyl-6,6a,7,8-tetrahydro-6H-dibenzo[b,d]pyran-9-one. Reduction of the $\Delta^{10(10a)}$ double bond afforded predominantly dl-trans-1-hydroxy-3-substituted-6,6-dimethyl-6,6a,7,8,10,10a-hexahydro-9H-dibenzo[b,d]pyran-9-one, with only minor quantities of the corresponding dl-6a,10a-cis isomer being formed.

While the dl-cis-1-hydroxy-3-substituted-6,6-dimethyl-6,6a,7,8,10,10a-hexahydro-9H-dibenzo[b,d]pyran-9-ones are pharmacologically active, their activity is less than that of the corresponding trans derivatives. The cis compounds are, however, useful as intermediates leading to pharmacologically active trans isomers. It recently has been discovered, for example, that reaction of a dl-cis-dibenzo[b,d]pyran-9-one derivative with aluminum chloride or aluminum bromide in a solvent such as dichloromethane effects complete isomerization to afford the corresponding dl-trans-derivative. Such dl-trans-1-hydroxy-3-substituted-6,6-dimethyl-6,6a,7,8,10,10a-hexahydro-9H-dibenzo[b,d]-pyran-9-ones recently have been found to be effective in the treatment of anxiety and depression, as described for example in U.S. Pat. Nos. 3,928,598, 3,944,673, and 3,953,603.

It is an object of this invention to provide a one-step process for preparing substantially exclusively dl-cis-1-hydroxy-3-substituted-6,6-dimethyl-6,6a,7,8,10,10a-hexahydro-9H-dibenzo[b,d]pyran-9-ones from readily available starting materials. Such compounds can then be converted to the corresponding more active dl-trans isomers.

SUMMARY OF THE INVENTION

This invention relates to a process involving the reaction of a 1-alkoxy-4-(1-hydroxy-1-methylethyl)-1,4-cyclohexadiene with a 5-substituted resorcinol to provide substantially exclusively a dl-cis-dibenzo[b,d]pyran-9-one derivative. More particularly, the invention provides a process for preparing a hexahydrodibenzopyranone compound of the formula

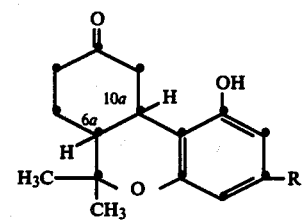

wherein R is $C_5$–$C_{10}$ alkyl, $C_5$–$C_{10}$ alkenyl, $C_5$–$C_8$ cycloalkyl, or $C_5$–$C_8$ cycloalkenyl; and wherein the hydrogen atoms attached at the 6a and 10a positions are oriented cis to one another; comprising reacting a 1-alkoxy-4-(1-hydroxy-1-methylethyl)-1,4-cyclohexadiene having the formula

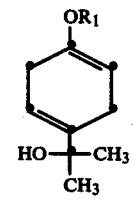

wherein $R_1$ is $C_1$–$C_4$ alkyl, with a 5-substituted resorcinol having the formula

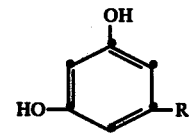

wherein R has the above-defined meaning; in the presence of a catalyst selected from the group consisting of boron tribromide, boron trifluoride, and stannic chloride, in an organic solvent at a temperature ranging from about −30° C. to about 100° C., for a period of time of from about 0.5 to about 8 hours.

DETAILED DESCRIPTION OF THE INVENTION

This invention provides a convenient process for preparing a dl-6a,10a-cis-hexahydro-dibenzo[b,d]pyran-9-one. As used herein, the term "6a,10a-cis" refers to the orientation relative to one another of the hydrogen atoms attached at the 6a and 10a positions of a dibenzopyranone compound represented by the above formula. Accordingly, compounds which are designated as being "6a,10a-cis" are those compounds of the above formula wherein the hydrogen atoms attached at the 6a and the 10a positions are oriented on the same side of the plane of the molecule. It will be recognized that at least two isomers are included by the "6a,10a" designation. In particular, both the 6a hydrogen atom and the 10a hydrogen atom can be oriented above the plane of the molecule, in which case their absolute configuration is designated as 6aβ and 10aβ. Alternatively, both the 6a hydrogen atom and the 10a hydrogen atoms can be oriented below the plane of the molecule, in which case they are designated as 6aα and 10aα.

The absolute configuration of the 6a-hydrogen atom and the 10a-hydrogen atom will not hereinafter be designated; rather, it is to be understood that the designation "6a,10a-cis" includes the separate mirror image isomers of the compounds having the above general formula, as well as a mixture of such mirror image isomers. For example, a 6a,10a-cis compound prepared by the process of this invention will be understood to include the 6aα,10aα-isomer, as well as the 6aβ,10aβ isomer, or a mixture of said mirror images. Such mixture of mirror image isomers will be designated in the normal manner as a dl-mixture, and is the usual product of the present process.

The product produced according to the process of this invention is substantially exclusively the dl-6a,10a-cis-isomer of a 1-hydroxy-3-substituted-6,6-dimethyl-6,6a,7,8,10,10a-hexahydro-9H-dibenzo[b,d]pyran-9-one, although small quantities on the order of about 5 to about 15 percent by weight of the corresponding dl-6a,10a-trans isomer generally can be detected. Purification of such mixture to remove the trans isomers is unnecessary since the major product, the dl-cis-hexahydrodibenzopyranone, is generally transformed to the pure dl-trans isomer by treatment with an aluminum halide, as is described in more detail hereinbelow.

According to the process of the present invention, a dl-cis-1-hydroxy-3-substituted-6,6-dimethyl-6,6a,7,8,10,10a-hexahydro-9H-dibenzo[b,d]pyran-9-one is prepared by reacting approximately equimolar quantities of a 1-alkoxy-4-(1-hydroxy-1-methylethyl)-1,4-cyclohexadiene and a 5-substituted resorcinol in the presence of a catalyst selected from boron tribromide, boron trifluoride, and stannic chloride. An especially preferred catalyst is stannic chloride.

The substituent located at the 5-position of the resorcinol and at the 3-position of the dibenzo[b,d]pyran-9-one derivative formed therefrom according to the process of this invention is the same group and is designated in the above formulas as R. Accordingly, R is defined as a $C_5$–$C_{10}$ alkyl group, and includes groups such as n-pentyl, isohexyl, 1-methylhexyl, 1,2-dimethylheptyl, 1,1-dimethylheptyl, 1,2,3-trimethylheptyl, n-decyl, 1,1-dimethyloctyl, and 1-ethyl-1-methylhexyl. Additionally, R can be a $C_5$–$C_{10}$ alkenyl group, examples of which are 2-hexenyl, 3-heptenyl, 1-methyl-1-heptenyl, 1,2-dimethyl-1-heptenyl, 3-octenyl, 1-ethyl-2-octenyl, 1,1-dimethyl-3-octenyl, and related groups. In addition to alkyl and alkenyl groups, R can be either a $C_5$–$C_8$ cycloalkyl or a $C_5$–$C_8$ cycloalkenyl moiety. Typical cycloalkyl groups which R represents include cyclopentyl, cyclohexyl and cyclooctyl, while cycloalkenyl groups represented by R include 1-cyclohexenyl, 2-cycloheptenyl, 1-cyclooctenyl, and the like.

Examples of 5-substituted resorcinols which can be employed in the process of this invention include 5-n-pentylresorcinol, 5-n-hexylresorcinol, 5-(1-methyl-2-ethylhexyl)resorcinol, 5-(1,1-dimethyloctyl)resorcinol, 5-(1,2-dimethylbutyl)resorcinol, 5-(1-hexenyl)resorcinol, 5-(1,2-dimethyl-1-heptenyl)resorcinol, 5-(1-ethyl-2-octenyl)resorcinol, 5-cyclohexylresorcinol, 5-cycloheptylresorcinol, 5-(1-cyclopentenyl)resorcinol, 5-(1-cyclohexenyl)resorcinol, 5-(2-cycloheptenyl)resorcinol, and the like.

As hereinbefore noted, according to the novel process of this invention a 5-substituted resorcinol is commingled with a 1-alkoxy-4-(1-hydroxy-1-methylethyl)-1,4-cyclohexadiene in approximately equimolar quantities. As noted in the above formula representing the cyclohexadiene derivative, the alkoxy group substituted at the 1-position is a $C_1$–$C_4$ alkyloxy moiety. Typical $C_1$–$C_4$ alkoxy groups include methoxy, ethoxy, n-propoxy, isopropoxy, n-butoxy and isobutoxy.

While the resorcinol and cyclohexadiene derivatives typically are reacted in about equimolar quantities, the 5-substituted resorcinol can, if desired, be utilized in excess amounts ranging from about a 0.1 to about a 2 molar excess. The reaction is carried out in the presence of a catalyst selected from boron tribromide, boron trifluoride, and stannic chloride. The boron trifluoride typically is employed as the diethyl etherate, while stannic chloride is a preferred catalyst. The amount of catalyst incorporated in the reaction generally is an equimolar quantity or an amount slightly in excess on a molar basis of the 5-substituted resorcinol and of the cyclohexadiene derivative. For instance, the amount of catalyst used can range from about 0.1 to about a 5.0 molar excess; however, even larger excesses can be incorporated if desired.

The reaction is best conducted in an organic solvent, the particular solvent used not being critical to the process. Examples of solvents commonly used in the process include halogenated hydrocarbons such as dichloromethane, 1,1-dibromoethane, 1,2-dichloroethane, 1,2-dibromoethane, 1-bromo-2-chloroethane, 1-bromopropane, and chloropropane; aromatic solvents such as benzene, chlorobenzene, toluene, and xylene; as well as ethers such as diethyl ether, dimethyl ether, and methyl ethyl ether. Preferred solvents include the halogenated hydrocarbons, especially dichloromethane, and the aromatic solvents, particularly benzene.

The process can be carried out at any temperature ranging from about −30° C. to about 100° C., and is conveniently conducted at about −10° to about 40° C., and is most preferably carried out at about 0° to about 25° C. Another preferred temperature range is from about −20° C. to about 100° C. The reaction between the 5-substituted resorcinol and the 1-alkoxy-4-(1-hydroxy-1-methylethyl)-1,4-cyclohexadiene generally is substantially complete within about 0.5 to about 8.0 hours; however, longer reaction times are not detrimental to the process and can be utilized if desired.

The reaction between the cyclohexadiene derivative and the resorcinol derivative is believed to proceed through a benzoxocin intermediate, specifically a 2,7-dihydroxy-5-isopropylidene-9-substituted-2,6-methano-3,4,5,6-tetrahydro-2H-1-benzoxocin. When the reaction is carried out in the presence of zinc chloride as the catalyst, the sole product is such benzoxocin derivative.

The product of the process of this invention, a dl-6a,10a-cis-1-hydroxy-3-substituted-6,6-dimethyl-6,6a,7,8,10,10a-hexahydro-9H-dibenzo[b,d]pyran-9-one, can be readily isolated by simply washing the reaction mixture with an aqueous acid such as aqueous hydrochloric acid or aqueous sulfuric acid, or with an aqueous base, and with water. Evaporation of the reaction solvent then provides the desired dl-6a,10a-cis-dibenzo[d,b]pyranone derivative, which can be further purified if desired by standard methods such as chromatography or crystallization from solvents such as hexane and cyclohexane.

Examples of dl-cis-dibenzo[b,d]pyranones which are readily prepared according to the process of this invention include the following:

dl-cis-1-hydroxy-3-n-pentyl-6,6-dimethyl-6,6a,7,8,10,10a-hexahydro-9H-dibenzo[b,d]pyran-9-one;

dl-cis-1-hydroxy-3-(1,2-dimethylheptyl)-6,6-dimethyl-6,6a,7,8,10,10a-hexahydro-9H-dibenzo[b,d]pyran-9-one;

dl-cis-1-hydroxy-3-(1,1-dimethyl-2-octenyl)-6,6-dimethyl-6,6a,7,8,10,10a-hexahydro-9H-dibenzo[b,d]pyran-9-one;

dl-cis-1-hydroxy-3-(1,2-dimethyl-1-hexenyl)-6,6-dimethyl-6,6a,7,8,10,10a-hexahydro-9H-dibenzo[b,d]pyran-9-one;

dl-cis-1-hydroxy-3-cyclohexyl-6,6-dimethyl-6,6a,7,8,10,10a-hexahydro-9H-dibenzo[b,d]pyran-9-one;

dl-cis-1-hydroxy-3-(1-cycloheptenyl)-6,6-dimethyl-6,6a,7,8,10,10a-hexahydro-9H-dibenzo[b,d]pyran-9-one; and dl-cis-1-hydroxy-3-(2-cyclohexenyl)-6,6-dimethyl-6,6a,7,8,10,10a-hexahydro-9H-dibenzo[b,d]pyran-9-one.

The 5-substituted resorcinols which are a required starting material in the instant process are readily available, see for example Adams et al., J. Am. Chem. Soc., 70, 664 (1948). The 1-alkoxy-4-(1-hydroxy-1-methylethyl)-1,4-cyclohexadiene can be conveniently prepared from the commercially available p-alkoxyacetophenone. For example, reaction of a p-alkoxyacetophenone with methyl magnesium bromide provides a 1-alkoxy-4-(1-hydroxy-1-methylethyl)-benzene. Reduction of the latter compound by reaction with lithium in liquid ammonia affords the desired 1-alkoxy-4-(1-hydroxy-1-methylethyl)-1,4-cyclohexadiene in high yield. Such preparation is described more fully by Inhoffen et al., Ann. 674, 28–35 (1964).

As hereinbefore noted, the dl-6a,10a-cis-1-hydroxy-3-substituted-6,6-dimethyl-6,6a,7,8,10,10a-hexahydro-9H-dibenzo[b,d]pyran-9-ones prepared by the process of this invention are useful in the preparation of anti-anxiety and anti-depressant drugs. For example, dl-cis-1-hydroxy-3-(1,1-dimethylheptyl)-6,6-dimethyl-6,6a,7,8,10,10a-hexahydro-9H-dibenzo[b,d]pyran-9-one can be reacted with aluminum chloride in dichloromethane to effect complete isomerization to afford exclusively the corresponding dl-trans derivative, namely dl-trans-1-hydroxy-3-(1,1-dimethylheptyl)-6,6-dimethyl-6,6a,7,8,10,10a-hexahydro-9H-dibenzo[d,b]pyran-9-one. The latter compound is particularly effective in treating humans suffering from anxiety and/or depression when given at daily dosages ranging from about 0.1 to 100 mg.

The following detailed examples are presented to further illustrate the process of this invention.

EXAMPLE 1

1-Methoxy-4-(1-hydroxy-1-methylethyl)-1,4-cyclohexadiene.

A solution of 33.2 g. of 1-methoxy-4-(1-hydroxy-1-methylethyl)benzene dissolved in 500 ml. of ethyl alcohol was added dropwise over a one hour period to a stirred solution of 800 ml. of liquid ammonia containing 14.0 g. of lithium metal shavings and 200 ml. of tetrahydrofuran. Following complete addition of the 1-methoxy-4-(1-hydroxy-1-methylethyl)benzene to the reaction mixture, the mixture was stirred for fifteen minutes. The reaction mixture was diluted with ethyl alcohol, and then poured over 1000 g. of crushed ice. The aqueous reaction mixture next was extracted with diethyl ether. The ethereal extracts were combined, washed with saturated aqueous ammonium sulfate solution and with water, and dried. Removal of the solvent provided an oil, which was then distilled to provide 22 g. of 1-methoxy-4-(1-hydroxy-1-methylethyl)-1,4-cyclohexadiene. B.P. 85°–90° C. at 0.3 torr.

EXAMPLE 2

1-Ethoxy-4-(1-hydroxy-1-methylethyl)-1,4-cyclohexadiene.

To a stirred solution of 330 ml. of liquid ammonia containing 36 g. of 1-ethoxy-4-(1-hydroxy-1-methylethyl)-benzene and 65 ml. of ethyl alcohol was added portion-wise 5.2 g. of Lithium metal as small pieces over one hour. The reaction mixture was stirred for thirty minutes, and then diluted with 50 g. of ammonium chloride and 150 ml. of toluene. The reaction mixture was stirred and allowed to warm to room temperature, and then further diluted with 200 ml. of water. After separating the aqueous and organic layers, the aqueous portion was extracted with 100 ml. of fresh toluene. The organic portions were combined, washed with fresh water, dried, and the solvent was removed by evaporation under reduced pressure, providing 34.6 g. of the product as an oil. The oil was distilled to afford 26.0 g. of 1-ethoxy-4-(1-hydroxy-1-methylethyl)-1,4-cyclohexadiene. B.P. 74°–79° C. at 0.02 torr.

EXAMPLE 3

1-Isopropoxy-4-(1-hydroxy-1-methylethyl)-1,4-cyclohexadiene.

Reaction of 1-isopropoxy-4-acetylbenzene with methyl magnesium bromide afforded 1-isopropoxy-4-(1-hydroxy-1-methylethyl)benzene. A solution of 35 g. of 1-isopropoxy-4-(1-hydroxy-1-methylethyl)benzene in 65 ml. of ethyl alcohol and 300 ml. of liquid ammonia was stirred while 5 g. of Lithium metal in the form of small pieces was added portionwise over thirty minutes. The reaction mixture was stirred for an additional thirty minutes, and then was diluted with 150 ml. of toluene and 35 g. of ammonium chloride. The reaction mixture was stirred at room temperature for twelve hours, and then was further diluted with 200 ml. of water. The aqueous layer was separated and extracted with 100 ml. of fresh toluene. The toluene layers were combined, washed with water, dried, and concentrated by evaporation under reduced pressure. Distillation of the residue provided 22.8 g. of 1-isopropoxy-4-(1-hydroxy-1-methylethyl)-1,4-cyclohexadiene. B.P. 85°–87° C. at 0.02 torr.

EXAMPLE 4

Following the procedure set forth in Example 3, 1-isobutoxy-4-(1-hydroxy-1-methylethyl)benzene was reduced to provide 1-isobutoxy-4-(1-hydroxy-1-methylethyl)-1,4-cyclohexadiene. B.P. 90°–95° C. at 0.02 torr.

Analysis Calc. for $C_{13}H_{22}O_2$; Theory: C, 74.24; H, 10.54; O, 15.21; Found: C, 72.29; H, 10.25; O, 15.42.

EXAMPLE 5 dl-cis-1-Hydroxy-3-(1,1-dimethylheptyl)-6,6-dimethyl-6,6a,7,8,10,10a-hexahydro-9H-dibenzo[b,d]pyran-9-one.

Five milliliters of a commercial solution of boron trifluoride diethyl etherate was added in one portion to a stirred solution of 504 mg. of 1-methoxy-4-(1-hydroxy-1-methylethyl)-1,4-cyclohexadiene and 708 mg. of 5-(1,1-dimethylheptyl)resorcinol dissolved in 25 ml. of benzene. The reaction mixture was stirred at 25° C. for five hours, and then added to 75 ml. of 6N hydrochloric acid solution. The benzene was removed from the mixture by evaporation, and then the acidic solution was extracted several times with diethyl ether. The ethereal extracts were combined, washed with water and with an aqueous solution of sodium bicarbonate, and dried. Removal of the solvent by evaporation under reduced pressure provided the product as a solid, which was then recrystallized from hexane to afford 365 mg. of dl-cis-1-hydroxy-3-(1,1-dimethylheptyl)-6,6-dimethyl-6,6a,7,8,10,10a-hexahydro-9H-dibenzo[b,d]pyran-9-one. M.P. 153°–158° C.

EXAMPLE 6 dl-cis-1-Hydroxy-3-n-pentyl-6,6-dimethyl-6,6a,7,8,10,-10a-hexahydro-9H-dibenzo[b,d]pyran-9-one.

A solution of 2.66 g. of 1-methoxy-4-(1-hydroxy-1-methylethyl)-1,4-cyclohexadiene and 2.9 g. of 5-(n-pentyl)resorcinol (olivetol) dissolved in 110 ml. of dichloromethane was stirred and cooled to −5° C. while 4.2 ml. of stannic chloride was added to the mixture dropwise over five minutes. The temperature of the reaction mixture increased from −5° C. to 2° C. during the addition of the stannic chloride. Following complete addition of the stannic chloride, the reaction mixture was warmed to about 24° C. and was stirred at that temperature for seven hours. The reaction mixture then was washed with water and with 1N sodium hydroxide solution, and dried. Removal of the solvent by evaporation under reduced pressure provided an oil, which was crystallized from 10 ml. of n-hexane to afford 450 mg. of dl-cis-1-hydroxy-3-n-pentyl-6,6-dimethyl-6,6a,7,8,10,10a-hexahydro-9H-dibenzo[b,d]pyran-9-one. M.P. 120°–134° C.

EXAMPLE 7 dl-cis-1-Hydroxy-3-(1,2-dimethyl-1-heptenyl)-6,6-dimethyl-6,6a,7,8,10,10a-hexahydro-9H-dibenzo[b,d]pyran-9-one.

A solution of 1-methoxy-4-(1-hydroxy-1-methylethyl)-1,4-cyclohexadiene in dichloromethane containing 5-(1,2-dimethyl-1-heptenyl)resorcinol was stirred at 0° C. while stannic chloride was added in one portion. The reaction mixture was then stirred for four hours at 24° C., and then washed with hydrochloric acid and water. The solution was dried and the solvent was removed by evaporation under reduced pressure to provide dl-cis-1-hydroxy-3-(1,2-dimethyl-1-heptenyl)-6,6-dimethyl-6,6a,7,8,10,10a-hexahydro-9H-dibenzo[b,d]pyran-9-one.

EXAMPLE 8 dl-cis-1-Hydroxy-3-(1,1-dimethylheptyl)-6,6-dimethyl-6,6a,7,8,10,10a-hexahydro-9H-dibenzo[b,d]pyran-9-one.

A solution of 11.8 g. of 5-(1,1-dimethylheptyl)-resorcinol and 10.0 g. of 1-methoxy-4-(1-hydroxy-1-methylethyl)-1,4-cyclohexadiene in 200 ml. of commercial grade dichloromethane was cooled to 5° C. and stirred while 13 ml. of stannic chloride was added dropwise over forty minutes. Following complete addition of the stannic chloride, the reaction mixture was warmed to room temperature and was then stirred for an additional seven hours. The reaction mixture next was diluted with 200 ml. of water. The organic layer was separated, washed with 2N hydrochloric acid, with water, with 1N sodium hydroxide, and again with water. The organic solution was dried and the solvent was removed therefrom by evaporation under reduced pressure to provide a solid residue. The solid so formed was recrystallized from hexane to afford 11.0 g. of dl-cis-1-hydroxy-3-(1,1-dimethylheptyl)-6,6-dimethyl-6,6a,7,8,10,10a-hexahydro-9H-dibenzo[b,d]pyran-9-one, which was found by thin layer chromatography to be identical to the product of Example 5.

EXAMPLE 9 dl-cis-1-Hydroxy-3-(1,1-dimethylheptyl)-6,6-dimethyl-6,6a,7,8,10,10a-hexahydro-9H-dibenzo[b,d]pyran-9-one.

The process of Example 8 was followed, except that the mixture was cooled to −10° C. before the addition of the stannic chloride, and it was stirred for seven hours after the addition while the temperature was held between 0° C. and 5° C. The product was 11.2 g. of dl-6a,10a-cis-1-hydroxy-3-(1,1-dimethylheptyl)-6,6-dimethyl-6,6a,7,8,10,10a-hexahydro-9H-dibenzo[b,d]pyran-9-one, found to be identical to the product of Example 5 by thin layer chromatography.

EXAMPLE 10 dl-cis-1-Hydroxy-3-(1,1-dimethylheptyl)-6,6-dimethyl-6,6a,7,8,10,10a-hexahydro-9H-dibenzo[b,d]pyran-9-one.

The process of Example 8 was repeated again, excpet that the stannic chloride was added while the reaction mixture was at 5° C., and the mixture was stirred at reflux temperature for seven hours after the stannic chloride was added. The product was 9.9 g. of dl-cis-1-hydroxy-3-(1,1-dimethylheptyl)-6,6-dimethyl-6,6a,7,8,10,10a-hexahydro-9H-dibenzo[b,d]pyran-9-one, which was found to be identical to the product of Example 5 by thin layer chromatography.

EXAMPLE 11 dl-cis-1-Hydroxy-3-(1,1-dimethylheptyl)-6,6-dimethyl-6,6a,7,8,10,10a-hexahydro-9H-dibenzo[b,d]pyran-9-one.

Following the general process of Example 5, a 4.72 g. portion of 5-(1,1-dimethylheptyl)resorcinol was reacted with 4.32 g. of 1-ethoxy-4-(1-hydroxy-1-methylethyl)-1,4-cyclohexadiene in 100 ml. of cyclohexane-stabilized dichloromethane (commercial grade dichloromethane). The reactants were dissolved in the dichloromethane and cooled to 0° C. before the dropwise addition of 6 ml. of stannic chloride. The mixture was stirred at 5° C. for 6 hours, and the reaction mixture was worked up as described in Example 5. The residue was slurried in 25 ml. of hot hexane, chilled and the collected precipitate was identified as 3.65 g. of dl-6a,10a-cis-1-hydroxy-3-(1,1-dimethylheptyl)-6,6-dimethyl-6,6a,7,8,10,10a-hexahydro-9H-dibenzo[b,d]-pyran-9-one, identified by thin-layer chromatography as identical to the product of Example 5.

EXAMPLE 12 dl-cis-1-Hydroxy-3-(1,1-dimethylheptyl)-6,6-dimethyl-6,6a,7,8,10,10a-hexahydro-9H-dibenzo[b,d]pyran-9-one.

The process of Example 11 was repeated, except that the resorcinol was reacted with 4.7 g. of 1-isopropoxy-4-(1-hydroxy-1-methylethyl)-1,4-cyclohexadiene, only 3.5 ml. of stannic chloride was used, and the stannic chloride was added while the reactants were at −10° C. The product was 2.65 g. of dl-cis-1-hydroxy-3-(1,1-dimethylheptyl)-6,6-dimethyl-6,6a,7,8,10,10a-hexahydro-9H-dibenzo[b,d]pyran-9-one, identified as identical to the product of Example 5 by thin-layer chromatography.

EXAMPLE 13 dl-cis-1-Hydroxy-3-(1,1-dimethylheptyl)-6,6-dimethyl-6,6a,-7,8,10,10a-hexahydro-9H-dibenzo[b,d]pyran-9-one.

A solution of 5.04 g. of 1-isobutoxy-4-(1-hydroxy-1-methylethyl)-1,4-cyclohexadiene in 100 ml. of commercial grade dichloromethane containing 4.72 g. of 5-(1,1-dimethylheptyl)resorcinol was cooled to −10° C. and stirred while 3.5 ml. of stannic chloride was added dropwise over five minutes. The temperature of the reaction mixture rose to 0° C. during the addition of the stannic chloride. The reaction mixture then was stirred at 0° C. for six and one half hours, and then washed with water, twice with 1N sodium hydroxide and again with water. The organic solution was dried and the solvent was removed therefrom by evaporation under reduced pressure to provide a solid product. The solid so formed was recrystallized from 25 ml. of hot hexane to afford 2.31 g. of dl-cis-1-hydroxy-3-(1,1-dimethylheptyl)-6,6-dimethyl-6,6a,7,8,10,10a-hexahydro-9H-dibenzo[b,d]-pyran-9-one, shown by thin layer chromatography to be identical to the product formed in Example 5.

EXAMPLE 14 dl-trans-1-Hydroxy-3-(1,1-dimethylheptyl)-6,6-dimethyl-6,6a,7,8,10,10a-hexahydro-9H-dibenzo[b,d]pyran-9-one.

A solution of 1.0 g. of dl-cis-1-hydroxy-3-(1,1-dimethylheptyl)-6,6-dimethyl-6,6a,7,8,10,10a-hexahydro-9H-dibenzo[b,d]pyran-9-one in 40 ml. of commercial grade dichloromethane was stirred at 24° C. while 1.0 g. of aluminum chloride was added in one portion. The reaction mixture was stirred at 24° C. for five hours. The reaction mixture was then washed with 1N hydrochloric acid solution and with water. After drying the organic solution, the solvent was removed therefrom by evaporation under reduced pressure, providing 994 mg. of the product as a solid. The solid so formed was recrystallized from hexane to afford 761 mg. of dl-trans-1-hydroxy-3-(1,1-dimethylheptyl)-6,6-dimethyl-6,6a,7,8,10,10a-hexahydro-9H-dibenzo[b,d]-pyran-9-one. M.P. 160°–161° C.

EXAMPLE 15 dl-trans-1-Hydroxy-3-n-pentyl-6,6-dimethyl-6,6a,7,8,10,10a-hexahydro-9H-dibenzo[b,d]pyran-9-one.

A solution of 400 mg. of dl-cis-1-hydroxy-3-n-pentyl-6,6-dimethyl-6,6a,7,8,10,10a-hexahydro-9H-dibenzo-[b,d]pyran-9-one in 200 ml. of commercial grade dichloromethane was stirred at 24° C. while 600 mg. of aluminum chloride was added in one portion. The reaction mixture then was stirred at 24° C. for two hours. After washing the reaction mixture with water and then drying the organic solution, the solvent was removed by evaporation under reduced pressure, leaving the product as a solid. The solid so formed was recrystallized from n-hexane to afford 220 mg. of dl-trans-1-hydroxy-3-n-pentyl-6,6-dimethyl-6,6a,7,8,10,10a-hexahydro-9H-dibenzo[b,d]pyran-9-one. M.P. 146°–150° C.

We claim:

1. A process for preparing a compound of the formula

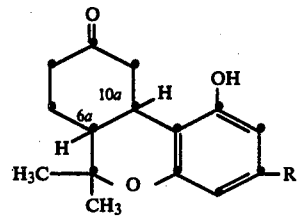

wherein:

R is $C_5$–$C_{10}$ alkyl, $C_5$–$C_{10}$ alkenyl, $C_5$–$C_8$ cycloalkyl, or $C_5$–$C_8$ cycloalkenyl; and wherein the hydrogen atoms attached at the 6a and the 10a positions are oriented cis to one another; which comprises reacting approximately equimolar quantities of a 1-alkoxy-4-(1-hydroxy-1-methylethyl)-1,4-cyclohexadiene of the formula

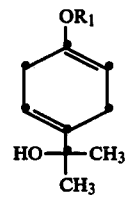

wherein $R_1$ is $C_1$–$C_4$ alkyl, with a 5-substituted resorcinol of the formula

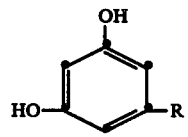

wherein R has the above-defined meaning; in the presence of a catalyst selected from the group consisting of boron tribromide, boron trifluoride, and stannic chloride, in an organic solvent at a temperature ranging from about −30° C. to about 100° C.

2. The process according to claim 1 wherein the organic solvent is selected from a halogenated hydrocarbon.

3. The process according to claim 1 wherein the temperature of the reaction ranges from about −20° C. to about 100° C.

4. The process according to claim 3 wherein the temperature of the reaction ranges from about −10° C. to about 40° C.

5. The process according to claim 4 wherein the temperature of the reaction ranges from about 0° C. to about 25° C.

6. The process according to claim 1 wherein the catalyst used is stannic chloride.

7. The process according to claim 6 wherein the solvent is a halogenated hydrocarbon and the reaction temperature ranges from about 0° to about 25° C.

8. The process according to claim 1 wherein in the resorcinol used, R is $C_5$–$C_{10}$ alkyl.

9. The process according to claim 1 wherein the cyclohexadiene derivative used is 1-methoxy-4-(1-hydroxy-1-methylethyl)-1,4-cyclohexadiene.

10. The process according to claim 1, said process comprising reacting 5-(1,1-dimethylheptyl)resorcinol with 1-methoxy-4-(1-hydroxy-1-methylethyl)-1,4-cyclohexadiene in the presence of stannic chloride in dichloromethane at a temperature ranging from about −10° C. to about 40° C. to provide dl-cis-1-hydroxy-3-(1,1-dimethylheptyl)-6,6-dimethyl-6,6a,7,8,10,10a-hexahydro-9H-dibenzo[b,d]pyran-9-one.

* * * * *